(12) United States Patent
Horacek et al.

(10) Patent No.: US 7,744,832 B2
(45) Date of Patent: Jun. 29, 2010

(54) INSTRUMENT CONTAINER HAVING MULTIPLE CHAMBERS WITH FLOW PATHWAYS THEREBETWEEN

(75) Inventors: Jeffrey R. Horacek, Mentor, OH (US); Christopher A. Jethrow, Maple Heights, OH (US)

(73) Assignee: American Sterilizer Company, Mentor, OH (US)

( * ) Notice: Subject to any disclaimer, the term of this patent is extended or adjusted under 35 U.S.C. 154(b) by 770 days.

(21) Appl. No.: 11/671,078

(22) Filed: Feb. 5, 2007

(65) Prior Publication Data

US 2008/0187465 A1    Aug. 7, 2008

(51) Int. Cl.
    *A61L 2/00* (2006.01)
(52) U.S. Cl. ...................................... 422/300; 422/297
(58) Field of Classification Search ........................ None
    See application file for complete search history.

(56) References Cited

U.S. PATENT DOCUMENTS

| | | | |
|---|---|---|---|
| 3,561,918 A | 2/1971 | Ray .............................. 21/84 |
| 5,266,275 A | 11/1993 | Faddis ........................ 422/116 |
| 5,346,075 A | 9/1994 | Nichols et al. ............. 211/60.1 |
| 5,534,221 A | 7/1996 | Hillebrenner et al. ......... 422/33 |
| 5,556,607 A | 9/1996 | Childers et al. ............. 422/300 |
| 5,711,921 A | 1/1998 | Langford ..................... 422/292 |
| 5,753,195 A | 5/1998 | Langford et al. ............ 422/292 |
| 5,906,802 A | 5/1999 | Langford .................... 422/300 |
| 6,015,529 A | 1/2000 | Lin et al. ...................... 422/28 |
| 6,030,579 A | 2/2000 | Addy et al. ................... 422/28 |
| 6,495,100 B1 | 12/2002 | Lin et al. ...................... 422/29 |
| 6,528,017 B2 | 3/2003 | Jacobs et al. .................. 422/33 |
| 6,596,232 B1 | 7/2003 | Lin et al. ...................... 422/28 |
| 6,685,895 B1 | 2/2004 | Lin et al. .................... 422/297 |
| 7,373,959 B2 * | 5/2008 | Edwards et al. ............. 220/265 |
| 2002/0119075 A1 | 8/2002 | Jacobs et al. .................. 422/33 |
| 2003/0072701 A1 | 4/2003 | Lin et al. .................... 422/292 |
| 2003/0206827 A1 | 11/2003 | Lin et al. ...................... 422/33 |
| 2004/0062693 A1 | 4/2004 | Lin et al. .................... 422/297 |
| 2004/0105780 A1 | 6/2004 | Lin et al. ...................... 422/28 |
| 2006/0127289 A1 | 6/2006 | Selig et al. .................. 422/300 |

* cited by examiner

*Primary Examiner*—Walter D Griffin
*Assistant Examiner*—Timothy Cleveland
(74) *Attorney, Agent, or Firm*—Kusner & Jaffe; Michael A. Centanni (57) ABSTRACT

A multi-chamber instrument container for microbially deactivating medical, dental, veterinary and mortuary instruments and articles. A pressure differential between chambers causes fluid flow therebetween, thus flowing fluid through internal passages of instrument extending between the chambers.

44 Claims, 6 Drawing Sheets

INSTRUMENT CONTAINER HAVING MULTIPLE CHAMBERS WITH FLOW PATHWAYS THEREBETWEEN

FIELD OF THE INVENTION

The present invention relates generally to disinfection or deactivation of medical, dental, pharmaceutical, veterinary or mortuary instruments and devices, and more particularly, to an instrument container having multiple chambers with flow pathways therebetween.

BACKGROUND OF THE INVENTION

Medical, dental, pharmaceutical, veterinary or mortuary instruments and devices, are routinely exposed to blood or other body fluids during medical procedures. Following such procedures, a thorough cleaning and anti-microbial deactivation of the instruments is required before subsequent use. Liquid microbial deactivation systems are now widely used to clean and deactivate instruments that cannot withstand the high temperature of a steam deactivation system. Liquid microbial deactivation systems typically operate by exposing the instruments to a liquid deactivation fluid, such as peracetic acid or some other strong oxidant. In such systems, the instruments to be cleaned are typically placed in a container that is put inside a decontamination chamber of the deactivation system. During a deactivation cycle, liquid microbial deactivation fluid is circulated through the decontamination chamber and the container therein. It should be understood that the term "instrument," as used herein, includes, but is not limited to, articles, such as medical, dental, pharmaceutical, veterinary and mortuary instruments and devices.

In many existing liquid microbial deactivation systems, one or more conduits having respective connectors are directly connected to ports of a lumened instrument (e.g., an endoscope) in order to flow liquid microbial deactivation fluid therethrough. In this regard, liquid microbial deactivation fluid is pumped through the conduits, thereby flowing through internal pathways/passages of the lumened instrument to effect microbial deactivation therein. One drawback to this approach is that the proper connectors must be identified and selected for connection with the ports of the lumened instrument. Another drawback to this approach is that it can be difficult to put liquid microbial deactivation fluid in contact with the external surfaces of the lumened instrument that are engaged with the connectors.

The present invention overcomes the foregoing drawbacks, and provides an instrument container having multiple chambers with flow pathways therebetween.

SUMMARY OF THE INVENTION

In accordance with the present invention, there is provided an instrument container for microbially deactivating articles placed therein, the instrument container having multiple chambers with flow pathways therebetween.

According to another aspect of the present invention there is provided a container for holding an instrument to be microbially deactivated in a reprocessor; the container comprising: a tray having a bottom wall and a continuous side wall extending from the periphery of said bottom wall, said bottom wall and said side wall defining a cavity for receiving an instrument to be microbially deactivated; a first removable seal member including a first opening dimensioned to receive a portion of the instrument extending therethrough; a dividing wall in the tray for dividing said cavity into a first chamber and a second chamber; wherein said dividing wall includes at least one recess dimensioned to receive said first removable seal member; and a lid attachable to said tray to enclose said cavity.

According to still another aspect of the present invention, there is provided an instrument container for microbial deactivation of an instrument in a microbial deactivation process, the container comprising: a first chamber; a second chamber; a wall separating the first chamber from the second chamber; an opening formed in the wall; a seal member for substantially sealing said opening, wherein an instrument extends through said seal member; and at least one fluid pathway between said first and second chamber passing through said wall.

According to yet another aspect of the present invention, there is provided a system for microbially deactivating instruments, the system comprising: a circulation system for circulating a microbial deactivation fluid through a decontamination chamber that forms part of the circulation system; a container located within said decontamination chamber for holding at least one instrument to be microbially deactivated, said container comprising: a tray having a bottom wall and a continuous side wall extending from the periphery of said bottom wall, said bottom wall and said side wall defining a cavity for receiving an instrument to be microbially deactivated; a first removable seal member including a first opening dimensioned to receive a portion of the instrument extending therethrough; a dividing wall in the tray for dividing said cavity into a first chamber and a second chamber; wherein said dividing wall includes at least one recess dimensioned to receive said first removable seal member; and a lid attachable to said tray to enclose said cavity.

An advantage of the present invention is the provision of a multi-chamber instrument container, wherein a pressure differential is maintained between the chambers to induce liquid microbial deactivation fluid to flow through internal pathways of an instrument located therein.

Another advantage of the present invention is the provision of a multi-chamber instrument container for microbially deactivating instruments placed therein, the container eliminating the need to connect ports of the instruments to connectors of a liquid deactivation fluid conduit, Still another advantage of the present invention is a multi-chamber instrument container that can be configured to simultaneously process instruments of varying dimensions.

Yet another advantage of the present invention is a multi-chamber instrument container that includes a flowable seal between the chambers.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, an embodiment of which will be described in detail in the specification and illustrated in the accompanying drawings which form a part hereof, and wherein.

DETAILED DESCRIPTION OF PREFERRED EMBODIMENT

Figure 1:
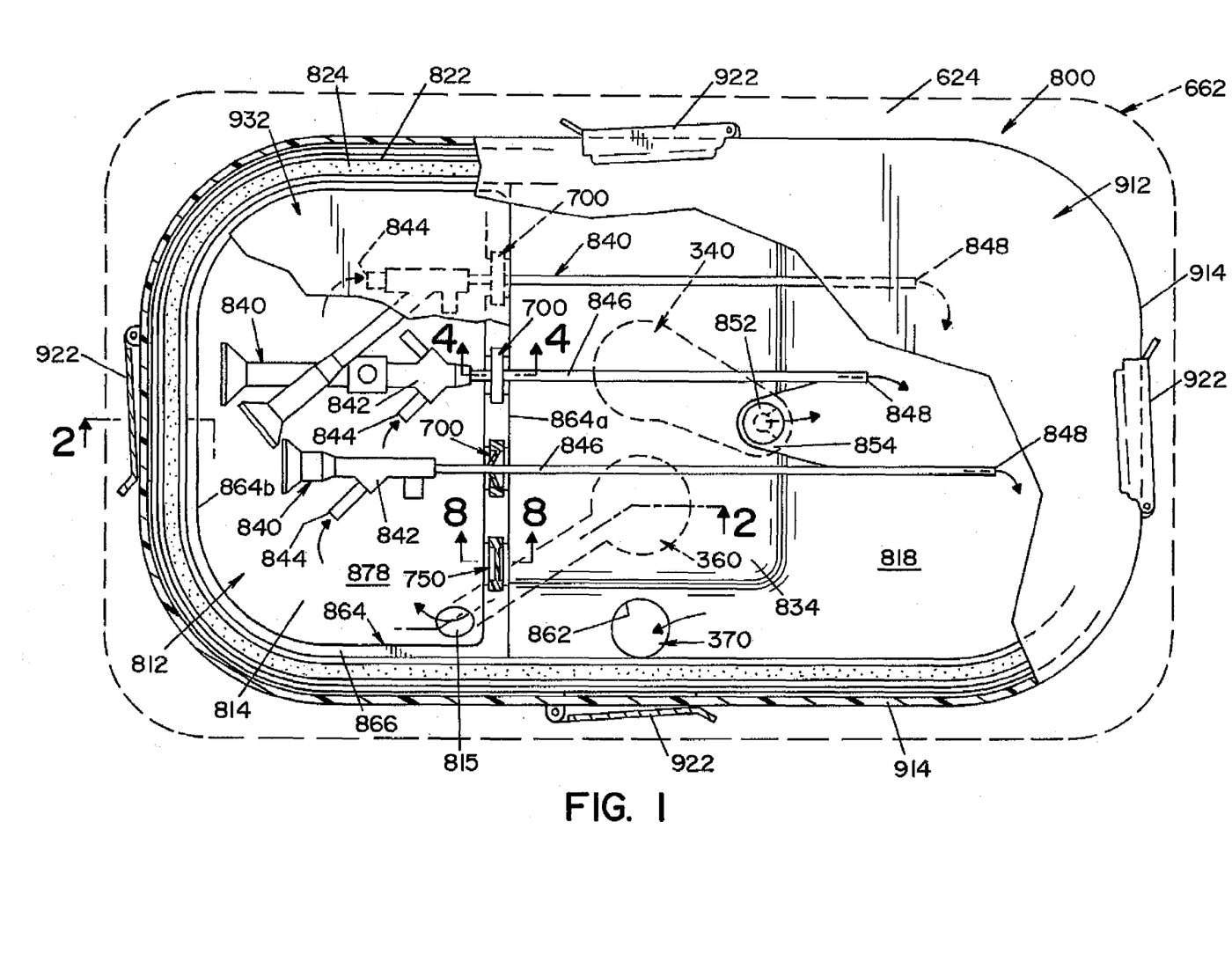
FIG. 1 is a top plan view, partially in section, of a multi-chamber instrument container according to an embodiment of the present invention.
Figure 2:
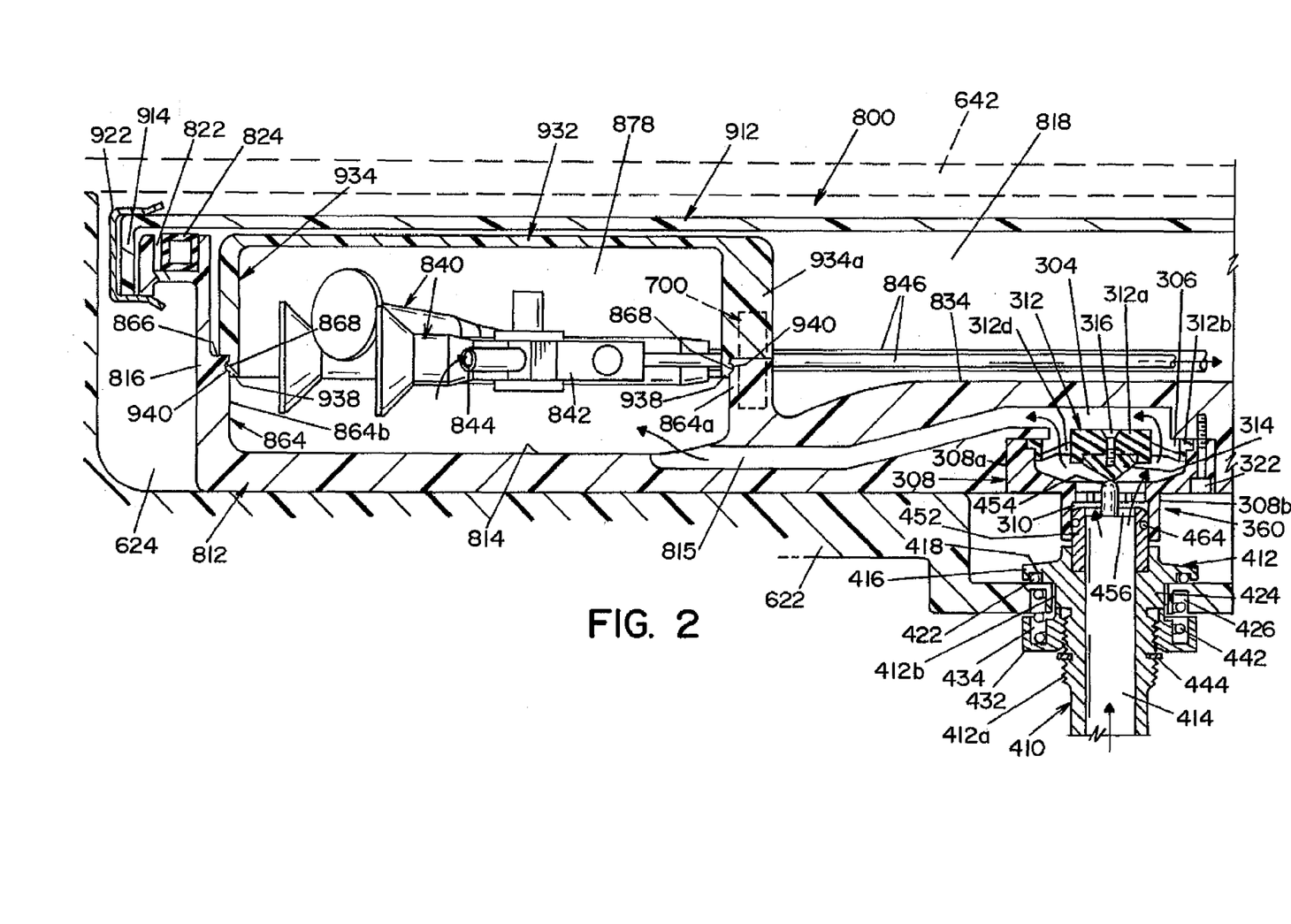
FIG. 2 is a sectional view of the multi-chamber instrument container, taken along lines 2-2 of FIG. 1.

Referring now to the drawings wherein the showings are for the purpose of illustrating an embodiment of the invention only, and not for the purpose of limiting same, FIGS. 1 and 2 show an instrument container 800 according to an embodiment of the present invention. Instrument container 800 is generally comprised of tray 812 and lid 912 that is attachable to tray 812. Tray 812 is generally cup-shaped and has a bottom wall 814 and a continuous side wall 816 that extends about the periphery of bottom wall 814 to one side thereof. Bottom wall 814 and side wall 816 define a cavity or chamber 818 dimensioned to receive instruments 840 therein.

The upper edge of side wall 816 is shaped to define a channel 822, best seen in FIG. 2. Channel 822 extends continuously about the upper edge of side wall 816. Channel 822 is dimensioned to receive a continuous, flexible seal 824. In the embodiment shown, seal 824 is an inflatable seal. An air conduit (not shown) communicates with seal 824 by means of a fitting (not shown) that is mounted to instrument container 800.

Within chamber 818, bottom wall 814 includes a mounting pad 834. A directional spray nozzle 852 is mounted onto mounting pad 834. Spray nozzle 852 is disposed in a shallow fan-like recess 854 formed in mounting pad 834. Spray nozzle 852 is dimensioned to generate fan-like spray patterns within chamber 818.

Lid 912 is generally a flat, planar element that is shaped to cover and enclose the opened, upper end of tray 812. Lid 912 includes a downward-extending flange 914 that extends about the periphery of lid 912 and is dimensioned to capture the upper edge of side wall 816.

A locking device 922 is provided to secure lid 912 to tray 812. In the embodiment shown, locking device 922 is an elongated, channel-like element that is pinned at one end to tray 812. The channel defined in the locking device 922 is dimensioned to capture the upper edge of tray 812 and lid 912, as shown in FIG. 2.

An inner chamber 878, dimensioned to receive instruments 840, is defined within chamber 818 by an inner wall portion 864. An inner cover 932 encloses inner chamber 878. Inner wall portion 864 is comprised of a dividing wall section 864a and a side wall section 864b. In the illustrated embodiment, side wall section 864b is integral with side wall 816, and extends inward therefrom. Side wall 816 and side wall section 864b form a ledge 866. An inward facing channel 868 is located near the upper edge of inner wall portion 864.

Figure 6:
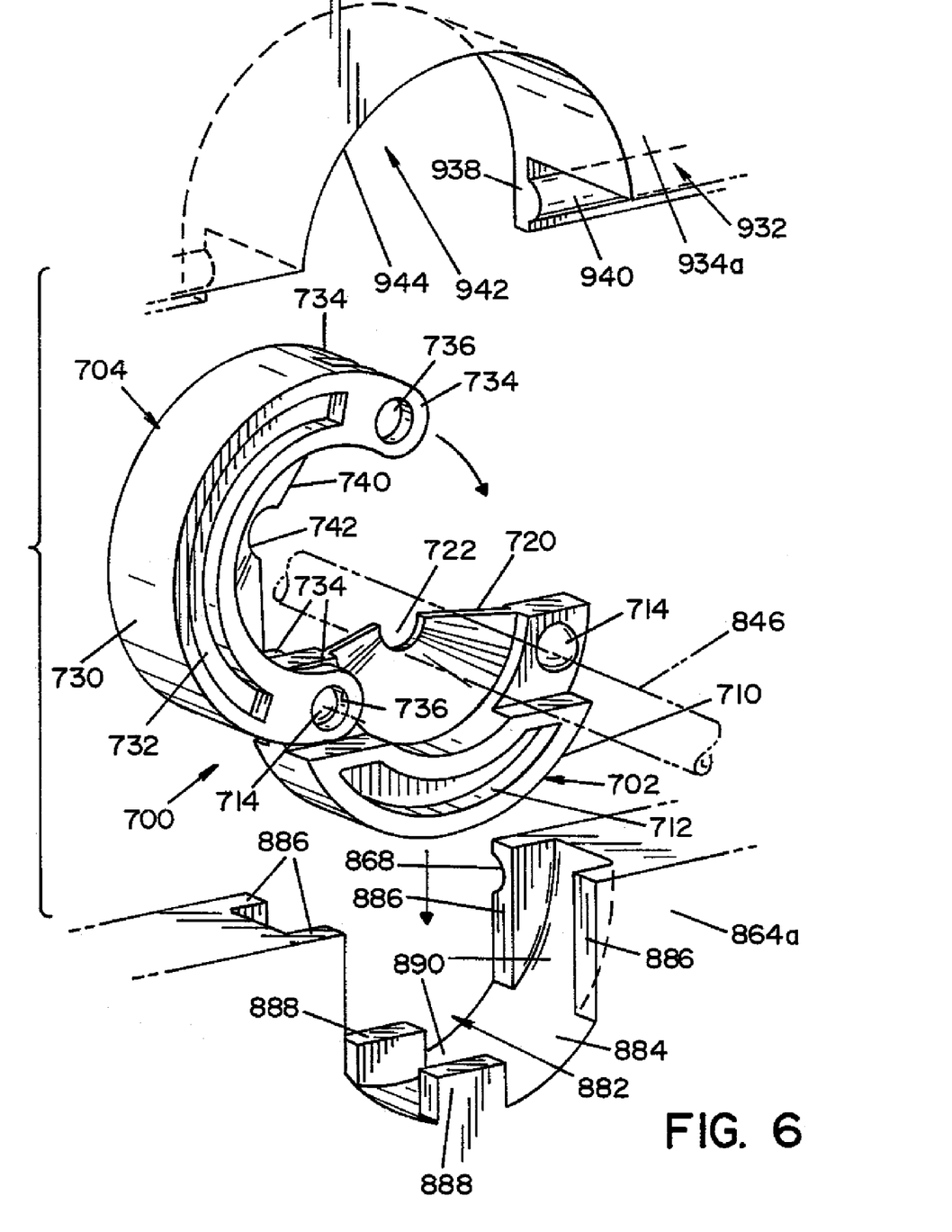
FIG. 6 is a perspective assembly view of a cover, a collet and a dividing wall section.

Dividing wall section 864a extends between opposing sections of side wall 816. As best seen in FIG. 6, dividing wall section 864a includes one or more recesses 882. In the embodiment shown, dividing wall section 864a has four recesses 882. Each recess 882 is defined by a semi-cylindrical surface 884. A pair of spaced apart wall sections 886 and a pair spaced apart tabs 888 define a slot 890 in each recess 882 that is dimensioned to capture a seal member, i.e., a collet assembly 700 or a plug 750, described in detail below.

Figure 4:
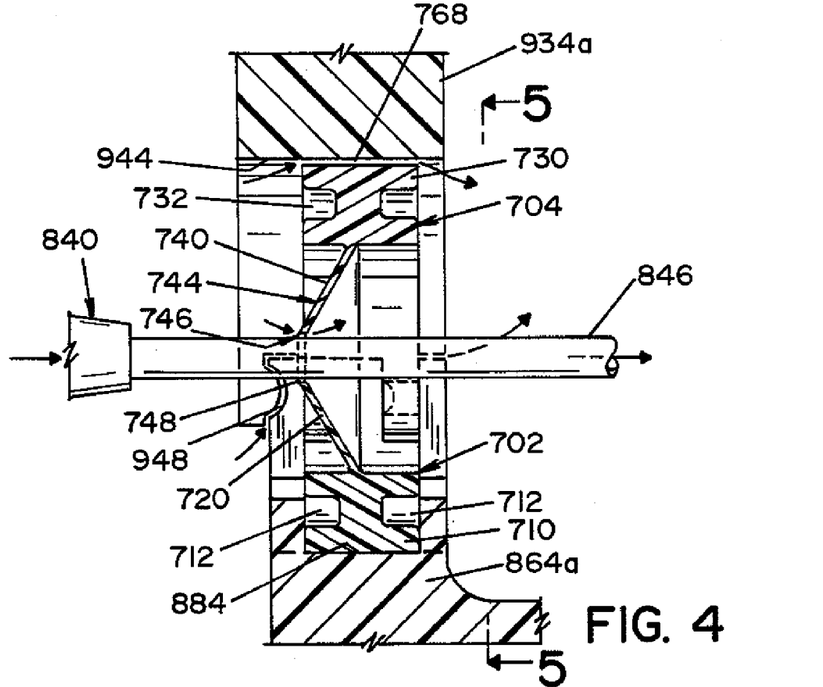
FIG. 4 is a sectional view of the multi-chamber instrument container, taken along lines 4-4 of FIG. 1, showing a cross-sectional view of a collet according to an embodiment of the present invention.
Figure 5:
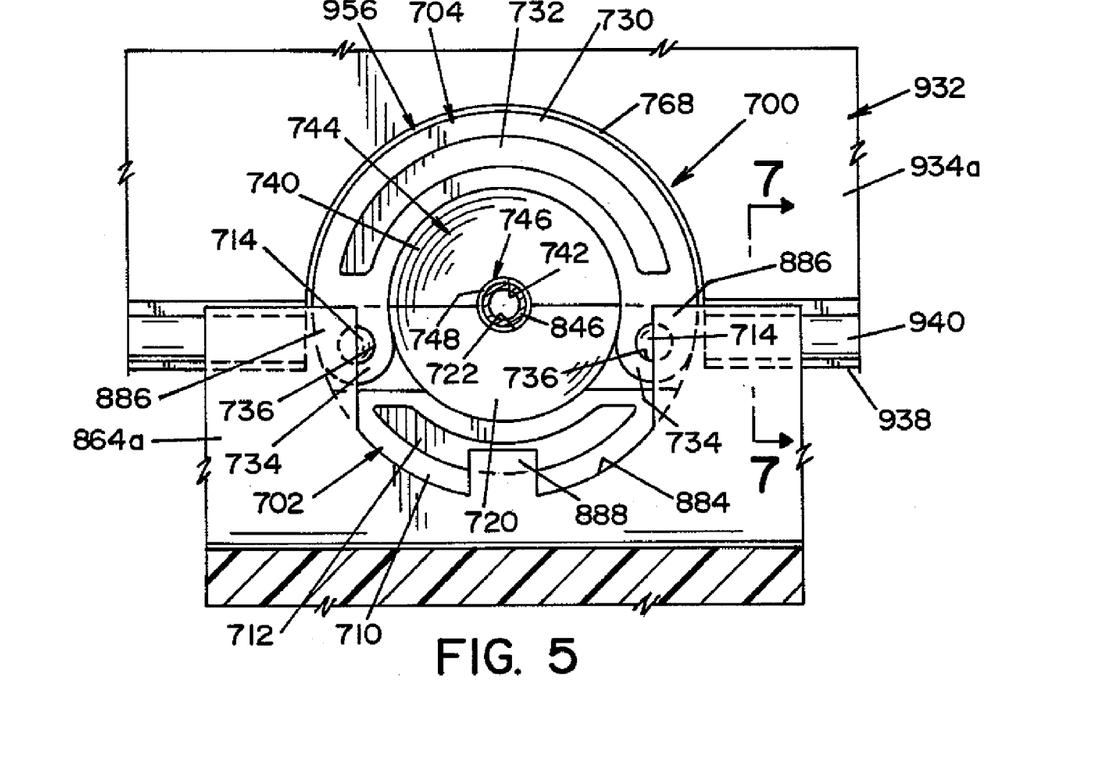
FIG. 5 is a partial sectional view of the multi-chamber instrument container, taken along lines 5-5 of FIG. 4, showing a front view of the collet.
Figure 8:
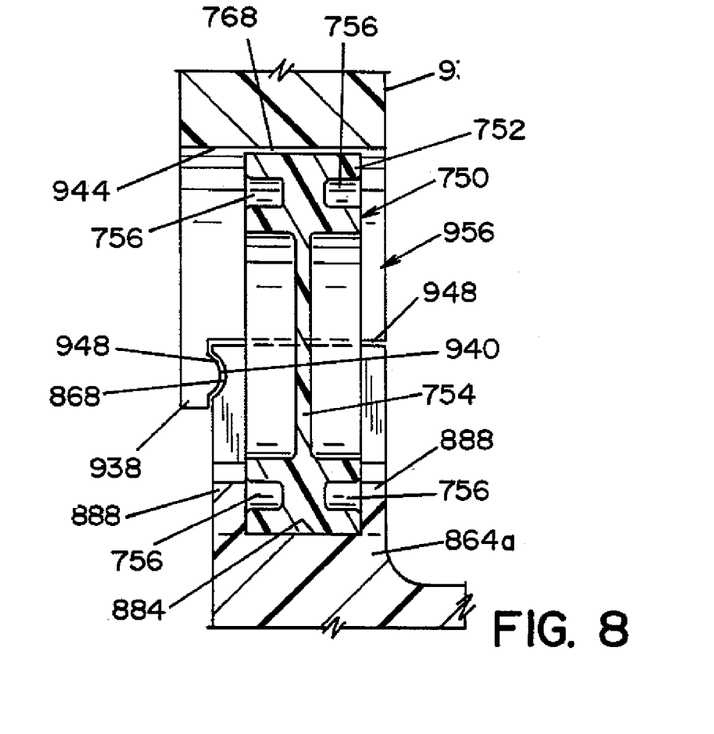
FIG. 8 is a sectional view taken along lines 8-8 of FIG. 1, showing a sectional view of a plug, according to an embodiment of the present invention.

A lid or cover 932 is generally a flat, planar element that is shaped to cover and enclose inner chamber 878. Cover 932 includes a downward-extending side wall 934 that extends about the periphery of cover 932. A flange 938 extends downward from the free edge of side wall 934. An outward extending rib 940 is formed in flange 938. As best seen in FIG. 6, one or more recesses 942 are formed in front side wall 934a. It will be appreciated that the number of recesses 942 formed in front side wall 934a correspond with the number of recesses 882 formed in dividing wall section 864a. Each recess 942 is defined by a semi-cylindrical surface 944. Cover 932 is secured to inner wall portion 864 to enclose inner chamber 878. In this regard, channel 868 formed in inner wall portion 864 is dimensioned to capture rib 940 of cover 932 in a snap-lock engagement. When cover 932 is secured to inner wall portion 864, recesses 942 of cover 932 and recesses 882 of dividing wall section 864a respectively abut to define a generally circular opening 956 dimensioned to receive a collet assembly 700 or a plug 750, as best seen in FIGS. 4, 5, and 8. Instruments 840 extend through openings 956, thereby extending across chambers 878 and 818, as will be discussed below.

Collet assembly 700 will now be described with reference to FIG. 6. Collet assembly 700 is comprised of a first collet section 702 and a second collet section 704. First collet section 702 includes a semi-cylindrical wall portion 710 and an inward extending collar 720. Protuberances 714 are formed at opposite ends of semi-cylindrical wall portion 710. In accordance with the illustrated embodiment, protuberances 714 are spherical shaped. Semi-cylindrical wall portion 710 may be molded to form arcuate cavities 712 in order to minimize the amount of material required to form collet assembly 700. Inward extending collar 720 is conically shaped, and includes a recess 722.

Second collet section 704 includes a semi-cylindrical wall portion 730 and an inward extending coller 740. A pair of spaced-apart fingers 734 are formed at opposite ends of semi-cylindrical wall portion 730. Openings 736 are formed in each finger 734, and are dimensioned to receive protuberances 714 of first collect section 702 in a snap-lock fashion. Semi-cylindrical wall portion 730 may be molded to form arcuate cavities 732 in order to minimize the amount of material required to form collet assembly 700. Inward extending collar 740 is conically shaped, and includes a recess 742.

By way of example and not limitation, first collet section 702 and second collet section 704 may be formed of such materials as acrylonitrile-butadiene-styrene (ABS) and polypropylene.

Collet assembly 700 is assembled by joining the ends of first and second collect sections 702, 704. In this respect, the ends of first and second collect sections 702, 704 are joined together by inserting protuberances 714 of first collet section 702 into openings 736 of second collet section 704. First collet section 702 can pivot around second collet section 704 after one end of first collet section 702 has been joined to second collet section 704 When collet assembly 700 is fully assembled as seen in FIGS. 5 and 6, inward extending collar 720 and inward extending collar 740 abut to define a conical portion 744, and recesses 722 and 742 abut to define a generally circular opening 746 extending through collet assembly 700 The circular opening formed by inward extending collars 720, 740 is dimensioned to receive a cylindrical portion (e.g., a tubular section) of an instrument 840, as will be described in further detail below.

Plug 750 includes a ring-shaped outer wall portion 752 and a generally planar disk-shaped center portion 754. In order to minimize the amount of material required to form plug 750, outer wall portion 752 may be molded to form arcuate cavities 756. Plug 750 has substantially the same dimensions as an assembled collet assembly 700.

In the embodiment shown, first and second fluid inlet assemblies 340, 360 (see FIG. 3) are formed in tray 812 to allow a microbial deactivation fluid to flow into instrument container 800. In this regard, first fluid inlet assembly 340 facilitates flow of a microbial deactivation fluid into chamber 818 through spray nozzles 852. Second fluid inlet assembly 360, shown in detail in FIG. 2, communicates with an internal passage 815, formed within bottom wall 814 of tray 812, to facilitate flow of microbial deactivation fluid to inner chamber 878. Fluid outlet assembly 370 (see FIG. 3) communicates with an opening 862, formed through bottom wall 814 within chamber 818, to facilitate flow of microbial deactivation fluid to a drain. Fluid inlet assemblies 340, 360 and fluid outlet assembly 370 are described in detail below.

It will be understood that the embodiment of instrument container 800 as illustrated herein is not intended to limit the scope of the present invention. For instance, according to an alternative embodiment of instrument container 800, chambers 878 and 818 may be arranged such that chamber 878 is located adjacent to chamber 818, rather than within chamber 818. Moreover, it is contemplated that instrument container 800 may have more than two internal chambers, with a dividing wall section 864a separating each chamber. Furthermore, the number of openings 956 formed by recesses 942 of cover 932 and recesses 882 of dividing wall section 864a may vary from the illustration shown in FIG. 1 to accommodate different numbers of instruments 840.

Figure 3:
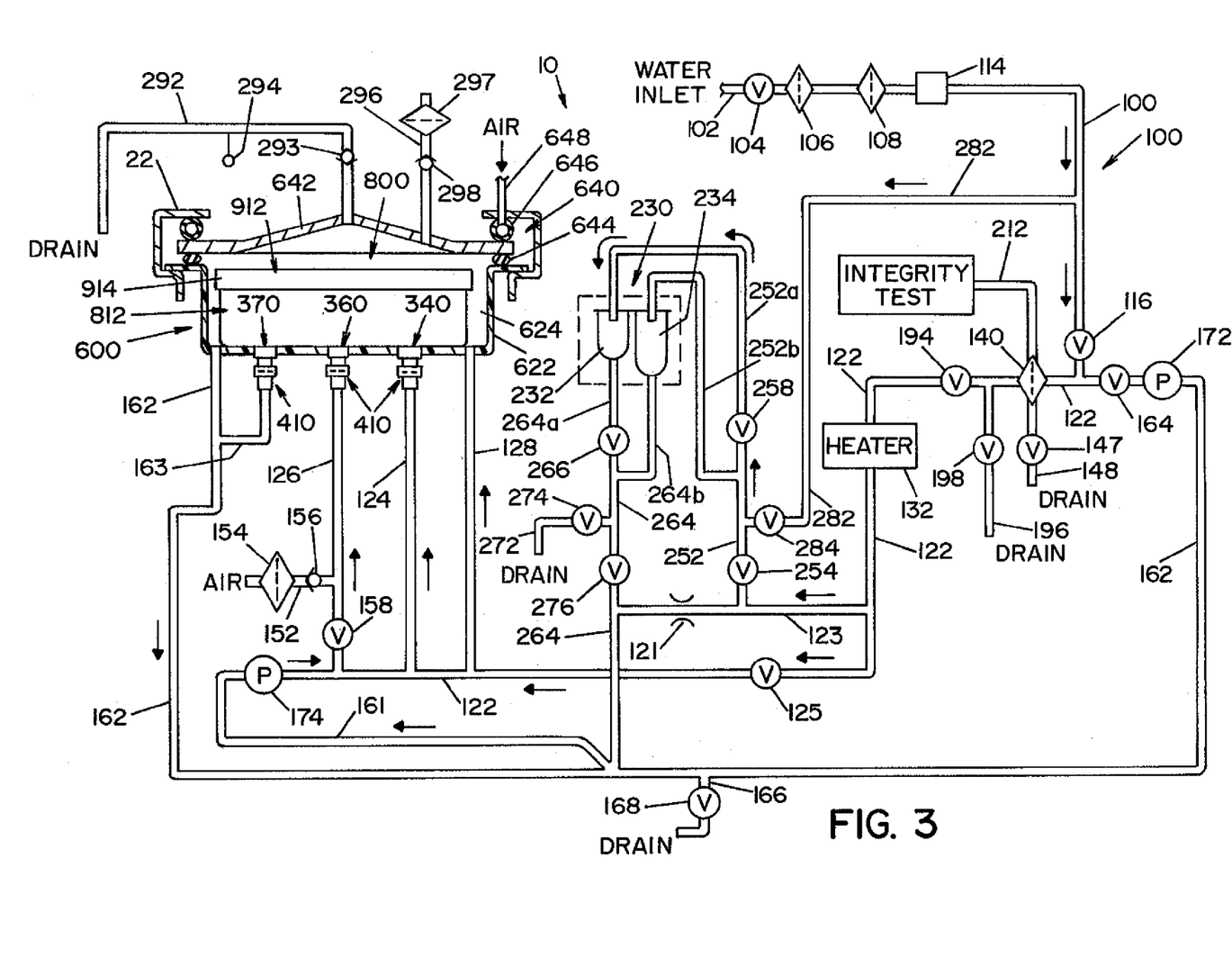
FIG. 3 is a schematic diagram of a reprocessor apparatus that is used in connection with the multi-chamber instrument container of the present invention, illustrating the fluid paths through the reprocessor apparatus.

Referring now to FIG. 3 there is shown a simplified, schematic piping diagram of an exemplary reprocessor apparatus 10 for microbially deactivating instruments using instrument container 800. Apparatus 10 is described herein to illustrate use of instrument container 800, and is not intended to limit the scope of the present invention.

Apparatus 10 includes a drawer assembly 600 that is movable between a closed position and an opened position. Drawer assembly 600 includes a drawer tray 622 that defines a recess or cavity 624. Cavity 624 is dimensioned to receive instrument container 800 according to the present invention.

A drawer sealing assembly 640 is disposed above drawer tray 622. Drawer sealing assembly 640 includes a plate 642 that is disposed above drawer tray 622. The dimensions of plate 642 generally correspond to the dimensions of drawer tray 622. A static seal 644 is disposed on the lower surface of plate 642. Static seal 644 is disposed about the periphery of cavity 624 in drawer tray 622, so as to engage the upper surface of drawer tray 622. An air-inflatable bladder 646 is disposed between plate 642 and a housing structure 22. An air line 648 is connected to bladder 646 to inflate and deflate the same. When inflated, bladder 646 is operable to force plate 642 downward toward drawer tray 622, wherein static seal 644 engages the upper surface of drawer tray 622 to form a seal about cavity 624 formed therein. When plate 642 is sealed against the upper surface of drawer tray 622, cavity 624 within drawer tray 622 defines a sealed decontamination chamber.

An overflow line 292 and a make-up air line 296 are attached to plate 642 and extend therethrough. In this respect, when plate 642 is in a sealing position against drawer tray 622, overflow line 292 and make-up air line 296 are in communication with the decontamination chamber defined between plate 642 and drawer tray 622.

One end of overflow line 292 is in communication with the decontamination chamber, and the other end of overflow line 292 is in communication with a drain source. A check valve 293 is disposed within overflow line 292 to allow the flow of fluid out of the decontamination chamber, but to restrict the flow of any fluid into the decontamination chamber through overflow line 292. A proximity sensor 294 is disposed within overflow line 292 downstream from directional check valve 293 to indicate when fluid is flowing therethrough.

A filter element 297 is disposed within make-up air line 296 to filter any air flowing into the decontamination chamber. In this respect, a directional check valve 298 is disposed within air make-up line 296 between filter element 297 and the decontamination chamber. Directional check valve 298 allows the flow of air into the decontamination chamber, but restricts the flow of air or fluid out of the decontamination chamber.

As schematically illustrated in FIG. 3, when instrument container 800 is disposed within cavity 624 in drawer tray 622, instrument container 800 is connected to fluid inlet lines and a fluid outlet line of a fluid circulation system 100, described in detail below. Instrument container 800 is also in communication with an air line (not shown) for inflating seal 824 disposed between tray 812 and lid 912.

Fluid circulation system 100, provides microbial deactivation fluid to the decontamination chamber defined by cavity 624 and is further operable to circulate the microbial deactivation fluid through the decontamination chamber, through instrument container 800 and through instruments 840 located within instrument container 800, as will be discussed below.

Fluid circulation system 100 includes a water inlet line 102 that is connected to a source of heated water (not shown). A valve 104 is disposed within water inlet line 102 to control the flow of water into apparatus 10. A pair of macro filters 106, 108 is provided in water inlet line 102 downstream from valve 104 to filter large contaminants that may exist in the incoming water. An ultraviolet (UV) treatment device 114 for deactivating organisms within the water source is preferably provided in water inlet line 102. A water valve 116 controls the flow of water from water inlet line 102 to a system feeder line 122.

System feeder line 122 includes a filter element 140 to filter microscopic organisms from the incoming water source to provide sterile water to fluid circulation system 100. A heater element 132 is disposed within system feeder line 122.

System feeder line 122 splits into a first branch feeder line 124, a second branch feeder line 126, and a third branch feeder line 128, downstream of heater element 132. A valve 125 is disposed within system feeder line 122 upstream of first, second and third branch feeder lines 124, 126, 128. First and second branch feeder lines 124, 126 communicate with instrument container 800 within cavity 624. First and second branch feeder lines 124, 126 are connected to container 800 through respective fluid inlet assemblies 340, 360, schematically illustrated in FIG. 3. Fluid inlet assemblies 340, 360 are adapted to operatively interact with valve actuating connectors 410, as shall be described in greater detail below. A third branch feeder line 128 is connected to cavity 624 of drawer tray 622.

An air line 152 is connected to second branch feeder line 126. Air line 152 is connected to a source (not shown) of dry air. A filter 154 is disposed within air line 152. A directional valve 156 is disposed within air line 152. Directional valve 156 is arranged to allow air to be forced into second branch feeder line 126, but to prevent water or fluids within second branch feeder line 126 from flowing toward the source of air. A valve 158 is disposed within second branch feeder line 126, between system feeder line 122 and where air line 152 connects to second branch feeder line 126.

A return line 162 is connected at one end to cavity 624 of drawer tray 622. The other end of return line 162 connects to the inlet side of a pump 172. Pump 172 is preferably a high pressure, low volume pump. The outlet side of pump 172 defines the beginning of system feeder line 122. A valve 164 is disposed within system feeder line 122 between pump 172 and the location where water inlet line 102 joins to system feeder line 122. A drain line 166 is connected to return line 162. A valve 168 is disposed within drain line 166 to control the flow of fluid therethrough.

A container return line 163 is connected at one end with container 800, through fluid outlet assembly 370, and is connected at the other end with system return line 162. Fluid outlet assembly 370 is adapted to operatively interact with a valve actuating connector 410. A return line 161 is connected at one end to system return line 162. The other end of return line 161 connects to the inlet side of a pump 174. The outlet side of pump 174 is connected to system feeder line 122. Pump 174 is preferably a high volume pump.

A drain line 196 is connected to system feeder line 122 between filter element 140 and heater element 132. A valve 198 is disposed within drain line 196 to regulate flow therethrough. A valve 194 is disposed in system feeder line 122 between heater element 132 and connection of drain line 196.

A drain line 148 is also connected to filter element 140. A valve 147 is disposed within drain line 148 to control the flow of fluid therethrough. A test line 212 is connected to filter element 140 to conduct integrity tests of filter element 140.

A connecting line 123 connects a chemistry inlet line 252 and a chemistry housing drain line 264 with system feeder line 122. A flow restrictor 121 is disposed in connecting line 123 between chemistry inlet line 252 and chemistry housing drain line 264.

Chemistry inlet line 252 is fluidly connected to a chemical delivery system 230, described below. A valve 254 is disposed in chemistry feed line 252 to control flow of fluid therethrough. Chemistry inlet line 252 splits into two sections 252a, 252b that both connect to chemistry delivery system 230. A connecting line 282 connects water inlet line 102 to chemistry inlet line 252. A valve 284 is disposed in connecting line 282.

Chemistry delivery system 230 is basically comprised of two side-by-side containers 232, 234. A valve 258 is disposed within section 252a of chemistry inlet line 252 to control the flow of fluid therethrough. Section 252a of chemistry inlet line 252 connects to a container 232 holding a chemical reagent (e.g., acetylsalicylic acid). Section 252b of chemistry inlet line 252 communicates with a container 234 holding builder components (e.g., a pre-salt, such as sodium perborate).

Chemistry housing outlet line 264 has a first section 264a connected to container 232 of chemistry delivery system 230, and a second section 264b connected to container 234 of chemistry delivery system 230. A valve 266 disposed within section 264a controls the flow of fluid from container 232. A drain line 272 connects to chemistry housing outlet line 264. A valve 274 is disposed in drain line 272 to control the flow of fluid therethrough. Downstream of drain line 272, a valve 276 is disposed in chemistry housing outlet line 264.

Fluid assemblies 340, 360 and 370 are adapted to operatively interact with valve actuating connectors 410. In a preferred embodiment of the present invention, valve actuating connectors 410 for fluid assemblies 340, 360 and 370 are substantially identical. Accordingly, only one valve actuating connector 410 shall be described in detail, it being understood that such description applies equally to the other valve actuating connectors 410.

Valve actuating connector 410 associated with second fluid inlet assembly 360 is shown in detail in FIG. 2. In the embodiment shown, valve actuating connector 410 has a cylindrical, tubular connector body 412 defining a fluid passage 414 therethrough. Connector body 412 has an outwardly extending, annular flange 416 formed at the free end thereof. Flange 416 has a downwardly facing annular groove 418 dimensioned to receive an O-ring 422. Connector body 412 includes a threaded portion 412a. Between flange 416 and threaded portion 412a is a cylindrical body portion 412b dimensioned to be received within a circular opening 424 within drawer tray 622. The diameter of opening 424 in drawer tray 622 is larger than the diameter of cylindrical body portion 412b of connector body 412. An annular groove 426 is formed around opening 424 in drawer tray 622. A threaded collar 432 is provided to secure connector body 412 to drawer tray 622. Collar 432 includes an annular groove 434 formed therein. Groove 434 in collar 432 is dimensioned to match annular groove 426 within drawer tray 622. A biasing element 442, in the form of a helical spring, is disposed within annular grooves 426, 434 formed within drawer tray 622 and threaded collar 432. Threaded collar 432 is maintained in position on connector body 412 by a retaining ring 444 disposed within an annular slot formed within connector body 412. The biasing effect of helical spring 442 causes flange 416 of tubular connector body 412 to force O-ring 422 into engagement with the upper surface of drawer tray 622. Valve actuating connector 410 is thus free to move a limited amount within cylindrical opening 424 in drawer tray 622. Opening 424 is at all times sealed by O-ring 422 that is forced into engagement with drawer tray 622 by the biasing effect of helical spring 442.

Cap 452 is inserted into a counter-bored opening formed in the free, upper end of connector body 412. Cap 452 is cylindrical in shape and includes an axially extending pin 454 at the end thereof. Openings 456 are formed through the end of cap 452 to communicate with fluid passage 414 defined by tubular connector body 412. An annular groove is formed within cap 452 to receive O-ring 464. Cap 452 is dimensioned to be received within opening 310 defined by sleeves on the respective fluid assemblies 340, 360 and 380 wherein O-ring 464 sealingly engages the inner surface of such sleeve. The lower end of connector body 412 is connected to, or forms part of, second branch feeder line 126 of fluid circulation system 100, as illustrated in FIG. 3.

Two other valve actuating connectors 410 are attached to drawer tray 622 to operatively engage first fluid inlet assembly 340 and fluid outlet assembly 370, as seen in FIG. 3. Connector body 412 of valve actuating connector 410 that is associated with first fluid inlet assembly 340 is connected to, or forms part of first branch feeder line 124. Connector body 412 of valve actuating connector 410 that is associated with fluid outlet assembly 370, is connected to, or forms part of, container return line 163.

Each of the aforementioned fluid assemblies 340, 360 and 370 is comprised of many like elements. A general understanding of the three fluid assemblies 340, 360 and 370 can be realized with reference to FIG. 2, wherein second fluid inlet assembly 360 on tray 812 of instrument container 800 is best seen.

With respect to fluid assembly 360, an inlet opening 304 is formed in bottom wall 814 of tray 812. Inlet opening 304 is in fluid communication with an internal passage 815, formed in bottom wall 814, that connects with inner chamber 878. An enlarged counter-sunk opening 306 is formed in the bottom surface of bottom wall 814 to receive a mounting plate 308. Mounting plate 308 is cylindrical in shape and has a cylindrical body portion 308a dimensioned to fit within counter-sunk opening 306 in tray 812. A cylindrical, tubular sleeve 308b extends downwardly from mounting plate 308. Sleeve 308b defines a cylindrical opening 310 that extends into a generally cup-shaped cavity formed in body portion 308a of mounting plate 308. A flexible valve element 312 is mounted to tray 812 by mounting plate 308.

Valve element 312 includes a cylindrical central body portion 312a that is connected to an outer, annular, flanged ring portion 312b by a plurality of radially extending arm portions (not shown) that define opening 312d. Valve element 312 is preferably formed of a resilient, flexible polymeric material and is preferably molded as an integral piece. A cylindrical recess is formed in the bottom of central body portion 312a to receive a rounded or domed cap element 314 formed of a hard, tough, durable polymeric material. Cap 314 is secured to central body portion 312a of valve element 312 by a conventional fastener 316. Flanged ring portion 312b of valve element 312 is dimensioned to be captured by a recess in mounting plate 308. Mounting plate 308 is attached to tray 812 within counter-sunk opening 306 by conventional fasteners 322.

Valve element 312 is molded or otherwise formed to assume a first, normal position, wherein central body portion 312a of valve element 312 engages or "seats" itself against the inner edge of mounting plate 308 that surrounds cylindrical bore 310, thereby effectively closing the opening through bottom wall 814 of tray 812. Valve element 312 is moveable to a second position, as shown in FIG. 2, wherein central body portion 312a of valve element 312 is moved away from mounting plate 308 to an opened position, and wherein a continuous fluid passage is formed through inlet opening 304, through openings 312d of valve element 312 and through sleeve portion 308b of mounting plate 308.

As indicated above, fluid assemblies 340 and 370 are substantially identical to fluid assembly 360. First fluid inlet assembly 340 communicates with spray nozzle 852 located within chamber 818, while fluid outlet assembly 370 communicates with drain opening 862 located within chamber 818.

Assembly of instrument container 800, for use with apparatus 10 to microbially deactivate instruments, will now be described with reference to FIGS. 1 and 2. It should be understood that although container 800 of the present invention can accommodate numerous types of instruments, container 800 is particularly advantageous for use in microbial deactivation of instruments having lumens, i.e., passages, extending therethrough (e.g., bronchoscopes and endoscopes). Accordingly, the illustrated embodiment of the present invention will be described in connection with such instruments.

The illustrated instrument 840 is comprised of a body portion 842 and a tubular portion 846. Body portion 842 includes one or more ports in fluid communication with one or more lumens or internal passages extending through tubular portion 846. Tubular portion 846 has at least one fluid outlet 848. It should be appreciated that the dimensions (e.g., length and outer diameter) of tubular portion 846 may vary.

A collet assembly 700 is assembled around tubular portion 846 of each instrument 840, as best seen in FIGS. 4-6. In this respect, protuberances 714 of first collect section 702 are snap-locked into openings 736 of second collect section 704. Tubular portion 846 extends though circular opening 746 formed by recesses 722, 742. It should be appreciated that collet assemblies 700 having circular openings 746 of various diameters may be provided in order to accommodate instruments 840 having tubular portions 846 of different outer diameters. Collet assemblies 700 are preferably selected to form a circular opening 746 having a diameter substantially equal to the outer diameter of the tubular portion 846 extending therethrough. A small annular gap 748 is formed between collet assembly 700 and the outer surface of tubular portion 846, thereby allowing microbial deactivation fluid to leak therethrough and contact with surfaces of collet assembly 700 and tubular portion 846 that define annular gap 748.

With lid 912 and cover 932 removed, one or more instruments 840 are placed within tray 812. An endoscope is located within tray 812 such that body portion 842 is located within inner chamber 878 and tubular portion 846 extends into chamber 818, as seen in FIGS. 1 and 2. With collet assembly 700 assembled around tubular portion 846 of the endoscope, first collet section 702 is inserted into slot 890 defined in dividing wall section 864a. Plugs 750 are inserted into any unused slots 890, as shown in FIGS. 1 and 8.

Figure 7:
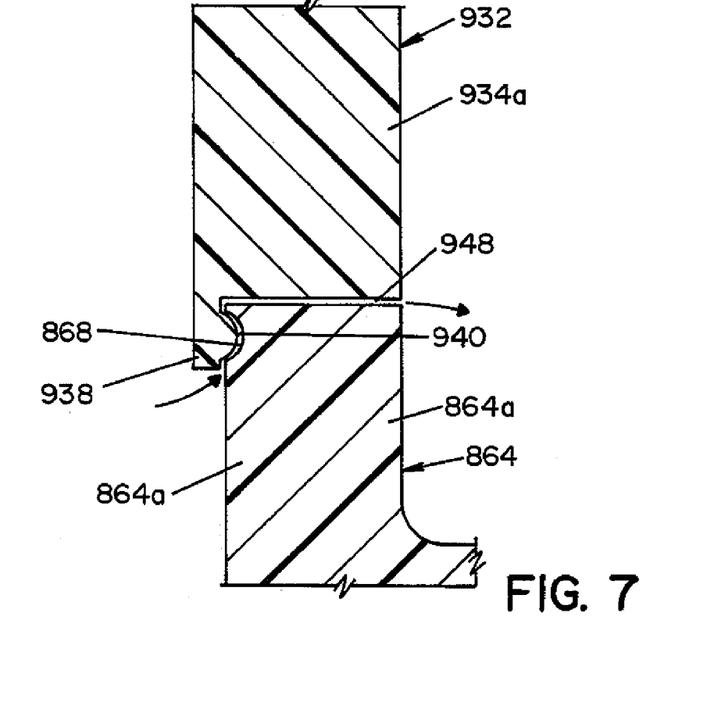
FIG. 7 is a sectional view taken along lines 7-7 of FIG. 5.

Inner cover 932 is oriented relative to inner chamber 878 such that recesses 942 of cover 932 face recesses 882 of inner chamber 878. Cover 932 is then secured to inner wall portion 864 by snap-lock engagement of rib 940 with channel 868, as seen in FIGS. 4-5 and 7-8. Microbial deactivation fluid can flow through a gap 948 formed between cover 932 and inner wall portion 864 (FIG. 7). Accordingly, microbial deactivation fluid contacts the outer surfaces defining gap 948.

Collet assembly 700 and plug 750 are dimensioned to form a generally annular gap 768 within each circular opening 956 defined by cover 932 and dividing wall section 864a. In this regard, the outer diameters of collet assembly 700 and plug 750 are preferably smaller than the diameter of circular openings 956. Accordingly, annular gap 768 allows microbial deactivation fluid to flow therethrough and contact with surfaces of collet assembly 700, plug 750, cover 932 and dividing wall section 864a that define annular gap 768.

Lid 912 is placed over tray 812 and is locked into position, using latch element 922 on tray 812. In addition to enclosing chamber 818, lid 912 also prevents disengagement of inner cover 932 from inner wall portion 864.

Following assembly of instrument container 800, a microbial deactivation operation may commence. Use of instrument container 800 in a microbial deactivation operation shall now be described in detail. As will be described below, to enable microbial deactivation fluid to be forced through the inner passages (e.g., lumens) of instruments 840, a higher pressure is generated inside inner chamber 878 than chamber 818. As a result of the pressure differential between chambers 878 and 818, microbial deactivation fluid is induced to flow through internal pathways of instruments 840. In this regard, microbial deactivation fluid enters instruments 840 through ports 844 of body portion 842 located within inner chamber 878, travels through internal passages, and exits through fluid outlet 848 located within chamber 818. The pressure differential will also cause the microbial deactivation fluid to flow through gaps 748 between collet assembly 700 and the outer surface of tubular portion 846 (see FIG. 4); gaps 768 between the outer surface of collet assembly 700 and cover 932 and dividing wall section 864a, located within circular opening 956 (see FIGS. 4 and 5); gaps 768 between the outer surface of plug 750 and cover 932 and dividing wall section 864*a*, located within circular opening 956 (see FIG. 8); and gap 948 between cover 932 and inner wall portion 864 (see FIG. 7).

With the instruments or items to be microbially decontaminated positioned within instrument container 800, as described above, an operator opens drawer assembly 600 of apparatus 10 to allow instrument container 800 to be placed within drawer tray 622.

A decontamination cycle for apparatus 10 includes a number of specific phases that shall now be described.

Preparation Phase

In preparation for a decontamination cycle, drawer assembly 600 is moved to an open position, and instrument container 800 with the instruments to be deactivated is placed within drawer tray 622. Instrument container 800 is oriented within cavity 624 of drawer tray 622 such that fluid inlet assemblies 340, 360 and fluid outlet assembly 370 on instrument container 800 align with the corresponding valve actuating connectors 410 within drawer tray 622. With instrument container 800 placed within drawer tray 622, drawer assembly 600 is moved to a closed position. During this user-preparation phase, chemistry containers 232 and 234 are inserted into chemical delivery system 230.

System-Seal Phase

With instrument container 800 within drawer tray 622 of drawer assembly 600 and drawer assembly 600 in a closed position, a decontamination cycle may be initiated. A first phase of the decontamination cycle is a system-sealing phase, wherein air is applied to inflatable bladder 646 above plate 642. Inflating bladder 646 forces static seal 644 on plate 642 down into engagement with the planar surface of drawer tray 622, thereby forming a complete seal around cavity 624 in drawer tray 622, and forming a sealed, decontamination chamber containing instrument container 800. Inflating bladder 646 is maintained throughout the decontamination cycle.

Fill Phase

With bladder 646 sealing instrument container 800 within the decontamination chamber, a fill phase is initiated. Valves 147, 168, 198 and 274 in drain lines 148, 166, 196 and 272, respectively, are in a closed position. Also closed are valves 284, 254 and 276 to the chemistry-delivery system 230. The remaining valves throughout apparatus 10 are opened to allow water from inlet line 102 to enter system feed line 122 and flow throughout fluid circulation system 100. Incoming water is first filtered by filter elements 106, 108 that remove macro particles above a certain size, such as 0.1 micron or above. Filter elements 106, 108 may be sized to successively filter out smaller-sized particles. Incoming water is then treated by UV treatment device 114 that applies ultra-violet (UV) radiation to the water to reduce levels of viruses therein. The incoming water then passes through valve 116 and enters fluid-circulation system 100. The incoming water is then filtered by filter element 140 within system feeder line 122 and proceeds to fill fluid-circulation system 100, the decontamination chamber, and instrument container 800.

The incoming water is under pressure from an external source and forces water in fluid-circulation system 100, the decontamination chamber, and instrument container 800. As a result of water entering the apparatus 10, air within the system will migrate toward overflow line 292 that is preferably disposed at the highest point of apparatus 10. Directional check valve 293 allows air and water to exit the decontamination chamber. The presence of water flowing through overflow line 292 is sensed by proximity sensor 294. Water flowing through drain line 292 is indicative that apparatus 10 is filled. The system controller then causes valves 104 and 116 to close, thereby stopping the flow of water into apparatus 10. The foregoing description basically describes the fill phase of a decontamination cycle.

Circulation Phase

Once apparatus 10 is filled with water, a system controller (e.g., a microcontroller or microprocessor) initiates a circulation phase to circulate water throughout fluid-circulation system 100. During the circulation phase, valves 254 and 276 to chemistry-delivery system 400 remain closed. Pumps 172 and 174 are energized to circulate water throughout fluid-circulation system 100, including the decontamination chamber and instrument container 800. Circulation of fluid within instrument container 800 and the decontamination chamber is described in detail below in connection with the "exposure phase."

The purpose of the circulation phase is to achieve the proper fluid temperature to deactivate the medical instruments in the instrument container. At periods throughout the fill phase and the circulation phase, heater 132 may be activated to increase the temperature of the water flowing throughout the system to maintain a desired fluid temperature.

Chemistry-Generation Phase

Following the circulation phase, valves 254 and 276 to chemistry-delivery system 230 are opened to allow the flow of water therethrough. Initially, valve 258 within section 252*a* of the chemistry-inlet line 252 is closed such that water initially flows into section 252*b* of chemistry-inlet line 252, wherein the water is directed into chemistry-delivery system 230. The chemical reagents within container 234 dissolve in the water and flow throughout the fluid-circulation system 100. Valve 266 in first section 264*a* of drain line 264 is also closed.

Following a pre-determined period of time, valve 258 and valve 266 are opened to allow water to flow through container 232. Container 232 preferably contains acetylsalicylic acid. Water flowing through container 232 exits chemistry-delivery system 230 through section 264*a* of chemistry housing outlet line 264.

Exposure Phase

During the exposure phase, the microbial deactivation fluid formed in the chemistry-generation phase is conveyed throughout fluid-circulation system 100. The microbial deactivation fluid flowing through first- and second-branch feeder lines 124, 126 flow into the decontamination chamber and into instrument container 800 therein. The deactivation fluid flowing into instrument container 800 via first branch feeder line 124 is sprayed into chamber 818 through spray nozzle 852 around the exterior of instruments 840. Fluid flowing through second branch feeder line 126 flows into inner chamber 878 of instrument container 800 through internal passage 815.

As fluid from branch feeder line 126 fills inner chamber 878, the pressure increases therein such that the pressure inside inner chamber 878 is greater than the pressure inside chamber 818. Consequently, fluid is induced to flow from inner chamber 878 into chamber 818 through the internal passages of instruments 840, via ports 844 of body portions 842. In this respect, fluid enters ports 844, travels through the internal passages, and exits instrument 840 through fluid outlet 848 located in chamber 818. The high pressure inside inner chamber 878 also forces fluid to flow from inner chamber 878 to chamber 818 through the gaps 748 surrounding the outer surface of tubular portion 846 extending through collet assemblies 700 (FIGS. 4 and 5) and through the gaps 768 surrounding the outer surface of collet assemblies 700 (FIGS. 4, 5, and 8) and plugs 750. Furthermore, fluid is forced through gap 948 between cover 932 and inner wall portion 864 (FIGS. 7 and 8). Fluid flows out of chamber 818 of instrument container 800 through drain opening 862, connected with container return line 163.

Deactivation fluid also flows into the decontamination chamber formed by drawer tray 622 and plate 642 via third branch feeder line 128; circulates through the decontamination chamber; and flows out of the decontamination chamber to system return line 162.

During the exposure period, pumps 172 and 174 continuously pump fluid throughout fluid-circulation system 100. Pump 172 is the high-pressure pump that provides sufficient pressure to force deactivation fluid through filter element 140 and through chemistry-delivery system 230. Pump 174, i.e., the high-volume pump, provides a larger amount of fluid at lower pressure to the decontamination chamber and the interior of instrument container 800. During the exposure phase, deactivation fluid is circulated throughout fluid-circulation system 100 and through the decontamination chamber and instrument container 800 for a pre-determined period of time.

Drain Phase

After a pre-determined exposure period, the system controller initiates a drain phase. The drain phase is comprised basically of two steps. During the drain phase, valves 254 and 276 to the chemical-delivery system 230 are closed to prevent flow thereto. Valves 168, 198, and 274 in drain lines 166, 196, and 272, respectively, are opened. Pumps 172, 174 continue to operate for a pre-determined period of time, forcing the deactivation fluid in the decontamination chamber and instrument container 800 out through drain lines 166, 196. At the same time, valve 284 is opened to connect chemistry-inlet line 252 to water-inlet line 102. Valve 104 is then opened to allow water to enter the system and flush chemistry-delivery system 230. Water entering chemistry-delivery system 230 is drained from fluid-circulation system 100 through drain line 272. After a pre-determined period of time sufficient to allow flushing of chemistry-delivery system 230 and after a period sufficient to allow draining of most of the fluid from fluid circulation system 100 through pumps 172, 174, pumps 172 and 174 are turned off. Valve 104 is closed to stop the flow of water to chemistry-delivery system 230. Valve 284 in connecting line 282 is then closed. Air line 152 is connected to a source of filtered, dry, pressurized air that enters inner chamber 878 of instrument container 800 through second branch feeder line 126. Thus, pressurized, dried air is conveyed through fluid-circulation system 100 to blow out remaining fluid within the internal passages of the instruments 840 in container 800. Inside container 800, the air follows the same fluid pathways as the microbial deactivation fluid, as described above in connection with the "exposure phase."

Once the drain phase has been completed, the air pressure to bladder 646 is removed to allow retraction of plate 642 and static seal 644 from the surface of drawer tray 622. Drawer assembly 600 may then be moved to an open position to allow removal of instrument container 800 from drawer tray 622. The deactivated instruments may remain within instrument container 800 and may be stored for a pre-determined period of time, with the instruments in instrument container 800 remaining in a microbially deactivated environment.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof Having described the invention, the following is claimed:

1. A container for holding an instrument to be microbially deactivated in a reprocessor; the container comprising:
   a tray having a bottom wall and a continuous side wall extending from the periphery of said bottom wall, said bottom wall and said side wall defining a cavity for receiving an instrument to be microbially deactivated;
   a dividing wall in the tray for dividing said cavity into a first chamber and a second chamber, said dividing wall including at least one recess formed therein;
   a first removable seal member including a first opening dimensioned to receive a portion of the instrument extending therethrough, said first removable seal member dimensioned to be received in said at least one recess in said dividing wall such that a first gap surrounds an outer surface of said first removable seal member, thereby providing a fluid pathway between said first chamber and said second chamber; and
   a lid attachable to said tray to enclose said cavity.

2. A container according to claim 1, wherein said lid encloses said first chamber and said second chamber.

3. A container according to claim 1, wherein said lid encloses said second chamber, said container further comprising a cover engageable with said dividing wall for enclosing said first chamber.

4. A container according to claim 3, wherein said cover is engageable with said dividing wall such that a second gap is defined therebetween, said second gap defining a fluid pathway that fluidly connects said first chamber to said second chamber.

5. A container according to claim 1, wherein said first chamber is located within said second chamber.

6. A container according to claim 1, wherein said first chamber is adjacent to said second chamber.

7. A container according to claim 1, wherein said first removable seal member is comprised of:
   a first section; and
   a second section attachable to said first section.

8. A container according to claim 1, wherein said first removable seal member includes a collar portion extending around said first opening dimensioned to receive said portion of the instrument.

9. A container according to claim 1, wherein said first opening dimensioned to receive said portion of the instrument extending therethrough has a diameter greater than the outer diameter of said portion of the instrument.

10. A container according to claim 1, wherein said container further comprises a second removable seal member dimensioned to be received in said recess of said dividing wall.

11. A container according to claim 10, wherein said container includes a fluid pathway between said first chamber and said second chamber, said fluid pathway includes a second gap surrounding an outer surface of said second removable seal member, when said second removable seal member is located within said recess of said dividing wall.

12. A container according to claim 1, wherein said first chamber includes a fluid inlet for receiving fluid into said first chamber.

13. A container according to claim 1, wherein said second chamber includes a fluid outlet for removing fluid from said second chamber.

14. A container according to claim 1, wherein a fluid pathway between said first chamber and said second chamber is defined by an internal passage of said instrument located between said first and second chambers.

15. A container according to claim 1, wherein said container includes a fluid pathway between said first chamber and said second chamber, said fluid pathway includes a second gap defined by said first removable seal member and the instrument extending therethrough.

16. An instrument container for microbial deactivation of an instrument in a microbial deactivation process, the container comprising:
- a first chamber;
- a second chamber;
- a wall separating the first chamber from the second chamber;
- an opening formed in the wall; and
- at least one removable seal member for substantially sealing said opening, wherein an instrument extends through said seal member, said at least one removable seal member dimensioned to be received in said opening in said wall such that a gap surrounds an outer surface of said at least one removable seal member, thereby providing a fluid pathway between said first chamber and said second chamber.

17. An instrument container according to claim 16, wherein said removable seal member comprises:
- a collet having an opening therein dimensioned to receive a portion of an instrument extending therethrough.

18. An instrument container according to claim 17, wherein said collet comprises:
- a first collet section; and
- a second collet section engageable with said first collet section.

19. An instrument container according to claim 16, wherein said container further comprises:
- cover means for enclosing the first and second chambers.

20. A device according to claim 19, wherein said cover means for enclosing the first and second chambers includes a first cover for enclosing said first chamber and a second cover for enclosing said second chamber.

21. An instrument container according to claim 16, wherein said first chamber is located within said second chamber.

22. A system for microbially deactivating instruments, the system comprising:
- a circulation system for circulating a microbial deactivation fluid through a decontamination chamber that forms part of the circulation system;
- a container located within said decontamination chamber for holding at least one instrument to be microbially deactivated, said container comprising:
  - a tray having a bottom wall and a continuous side wall extending from the periphery of said bottom wall, said bottom wall and said side wall defining a cavity for receiving an instrument to be microbially deactivated;
  - a dividing wall in the tray for dividing said cavity into a first chamber and a second chamber, said dividing wall including at least one recess formed therein;
  - a first removable seal member including a first opening dimensioned to receive a portion of the instrument extending therethrough, said first removable seal member dimensioned to be received in said at least one recess such that a first gap surrounds an outer surface of said first removable seal member, thereby providing a fluid pathway between said first chamber and said second chamber; and
  - a lid attachable to said tray to enclose said cavity.

23. A system according to claim 22, wherein said lid encloses said first chamber and said second chamber.

24. A system according to claim 22, wherein said lid encloses said second chamber, said container further comprising a cover engageable with said dividing wall for enclosing said first chamber.

25. A system according to claim 24, wherein said cover is engageable with said dividing wall such that a second gap is defined therebetween, said second gap defining a fluid pathway that fluidly connects said first chamber to said second chamber.

26. A system according to claim 22, wherein said first chamber is located within said second chamber.

27. A system according to claim 22, wherein said first chamber is adjacent to said second chamber.

28. A system according to claim 22, wherein said first removable seal member is comprised of:
- a first section; and
- a second section attachable to said first section.

29. A system according to claim 22, wherein said first removable seal member includes a collar portion extending around said first opening dimensioned to receive said portion of the instrument.

30. A system according to claim 22, wherein said first opening dimensioned to receive said portion of the instrument extending therethrough has a diameter greater than the outer diameter of said portion of the instrument.

31. A system according to claim 22, wherein said container further comprises a second removable seal member dimensioned to be received in said recess of said dividing wall.

32. A system according to claim 31, wherein said container includes a fluid pathway between said first chamber and said second chamber, said fluid pathway includes a second gap surrounding an outer surface of said second removable seal member, when said second removable seal member is located within said recess of said dividing wall.

33. A system according to claim 22, wherein said first chamber includes a fluid inlet for receiving fluid into said first chamber from the circulation system.

34. A system according to claim 22, wherein said second chamber includes a fluid outlet for removing fluid from said second chamber.

35. A system according to claim 22, wherein a fluid pathway between said first chamber and said second chamber is defined by an internal passage of said instrument located between said first and second chambers.

36. A system according to claim 22, wherein said container includes a fluid pathway between said first chamber and said second chamber, said fluid pathway includes a second gap defined by said first removable seal member and the instrument extending therethrough.

37. A container according to claim 1, wherein said at least one recess includes a slot dimensioned to capture said first removable seal member therein.

38. A container according to claim 37, wherein said slot is defined by a pair of spaced apart wall sections and a pair of spaced apart tabs.

39. A container according to claim 16, wherein said opening includes a slot dimensioned to capture said removable seal member therein.

40. A container according to claim 39, wherein said slot is defined by a pair of spaced apart wall sections and a pair of spaced apart tabs.

41. A container according to claim 22, wherein said at least one recess includes a slot dimensioned to capture said first removable seal member therein.

42. A container according to claim 41, wherein said slot is defined by a pair of spaced apart wall sections and a pair of spaced apart tabs.

43. A container according to claim 3, wherein said cover includes at least one recess formed therein, said at least one recess in said cover and said at least one recess in said dividing wall defining an opening dimensioned to receive said first removable seal member therein.

44. A container according to claim 24, wherein said cover includes at least one recess formed therein, said at least one recess in said cover and said at least one recess in said dividing wall defining an opening dimensioned to receive said first removable seal member therein.

* * * * *